(12) United States Patent
Wang et al.

(10) Patent No.: US 6,673,446 B2
(45) Date of Patent: *Jan. 6, 2004

(54) FLUSHABLE FIBER COMPOSITIONS COMPRISING MODIFIED POLYPROPYLENE AND MODIFIED POLY (ETHYLENE OXIDE) AND PROCESS FOR MAKING THE SAME

(75) Inventors: James H. Wang, Appleton, WI (US); David M. Schertz, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 82 days.

This patent is subject to a terminal disclaimer.

(21) Appl. No.: 09/840,017

(22) Filed: Apr. 23, 2001

(65) Prior Publication Data

US 2002/0022691 A1 Feb. 21, 2002

Related U.S. Application Data

(62) Division of application No. 09/208,947, filed on Dec. 9, 1998, now abandoned.
(60) Provisional application No. 60/070,249, filed on Dec. 31, 1997.

(51) Int. Cl.[7] .................... D01F 6/46; A61L 15/26; C08L 23/10; C08L 51/08; C08L 71/02
(52) U.S. Cl. ............... 428/372; 428/374; 442/201; 525/64; 525/187; 525/194
(58) Field of Search .................. 428/372, 376; 442/201; 525/64, 187, 194

(56) References Cited

U.S. PATENT DOCUMENTS

| | | | |
|---|---|---|---|
| 4,229,334 A | 10/1980 | Klabacka et al. | |
| 5,614,574 A * | 3/1997 | Sheth | 524/140 |
| 5,685,757 A | 11/1997 | Kirsch et al. | |
| 5,700,872 A | 12/1997 | Wang et al. | |
| 5,807,930 A * | 9/1998 | Wang et al. | 525/187 |
| 5,912,076 A * | 6/1999 | Wang et al. | 428/338 |
| 6,063,866 A * | 5/2000 | Wang et al. | 525/187 |
| 6,153,701 A * | 11/2000 | Potnis et al. | 525/191 |
| 6,255,386 B1 * | 7/2001 | Wang et al. | 525/187 |
| 6,359,063 B1 * | 3/2002 | Wang et al. | 525/187 |

FOREIGN PATENT DOCUMENTS

| | | |
|---|---|---|
| EP | 0080274 | 6/1983 |
| EP | 0210754 | 2/1987 |
| EP | 0436966 | 7/1991 |
| EP | 0438598 | 7/1991 |
| EP | 0612773 | 8/1994 |
| EP | 0705934 | 4/1996 |
| JP | 61-181859 | 8/1986 |
| WO | WO 94/17226 | 8/1994 |
| WO | WO 95/10645 | 4/1995 |
| WO | WO 96/20738 | 7/1996 |

OTHER PUBLICATIONS

Derwent Publications Ltd., Database WPI, JP 08 212995 (Misubishi Paper Mills Ltd.), Aug. 20, 1996.

Derwent Publications Ltd., Database WPI, JP 01 246411 (Sawashita A), Oct. 2, 1989.

* cited by examiner

*Primary Examiner*—D. R. Wilson
(74) *Attorney, Agent, or Firm*—Kilpatrick Stockton LLP

(57) ABSTRACT

A fiber composition which comprises a blend of modified polypropylene and modified poly(ethylene oxide). This fiber composition can be melt-processed to make fibers useful in flushable personal care products. A process for making this fiber composition is also provided.

10 Claims, 10 Drawing Sheets

FLUSHABLE FIBER COMPOSITIONS COMPRISING MODIFIED POLYPROPYLENE AND MODIFIED POLY (ETHYLENE OXIDE) AND PROCESS FOR MAKING THE SAME

CROSS REFERENCE TO RELATED APPLICATION

The present application is a divisional application of U.S. Ser. No. 09/208,947, filed on Dec. 9, 1998, now abandoned.

This application claims the benefit of U.S. Provisional Application Ser. No. 60/070,249, filed Dec. 31, 1997.

TECHNICAL FIELD

This invention relates to flushable fiber compositions. In a more specific aspect, this invention relates to flushable fiber compositions comprising modified polypropylene and modified poly(ethylene oxide). This invention also relates to a process for making such fiber compositions.

BACKGROUND OF THE INVENTION

Personal care products (such as diapers, sanitary napkins and adult incontinence garments) are generally constructed from a number of different components and materials. Such articles typically have a portion (usually the backing layer, liner or baffle) constructed of a liquid repellent film material. This film material is appropriately constructed to minimize or prevent the exudation of the absorbed liquid from the article and to obtain greater utilization of the absorbent capacity of the personal care product. Commonly used film materials include plastic materials such as polyethylene films and the like.

Although such personal care products are relatively inexpensive, sanitary and easy to use, the proper disposal of a soiled product is not without problems. With greater interest being placed in protecting the environment today, there is a need to develop materials that are more compatible with the existing and developing water disposal technologies while still delivering the performance which consumers have come to expect and demand. An ideal disposal alternative would be to use municipal sewage treatment and private residential septic systems. Products suited for disposal in sewage systems can be flushed down a convenient toilet and are termed "flushable." While flushing such articles would be convenient, the liquid repellent film material (which normally does not disintegrate in water) tends to plug toilets and sewer pipes. Therefore, although undesirable, a person must separate the barrier film material from the absorbent article prior to flushing.

In addition to the disposable article, the packaging in which the article is distributed is often made from a water resistant material. Water resistivity is necessary to prevent the degradation of the packaging from environmental conditions and to protect the disposable article contained in the packaging. Although this packaging may be safely stored with other refuse for commercial disposal, the packaging is preferably disposed of together within the toilet with the discarded disposable article. However, where such packaging is composed of a water resistant material, plugging of the drains to the toilet may result.

In an effort to overcome these deficiencies, two methods have been utilized in the industry. The first method is for hydrophilic materials to be treated with a hydrophobic material to impart the desired water resistant properties to the hydrophilic materials.

The second method has been to modify a water resistant polymer. One of the more useful ways of modifying polymers involves blending with other polymers of different structures and properties. In a few cases, polymer blend combinations are thermodynamically miscible and exhibit physical and mechanical compatibility. However, a greater number of blends are phase separated and generally exhibit poor mechanical compatibility. Phase separated blends can exhibit physical and mechanical compatibility where the polymer compositions are similar (for example, polyolefins blended with other similar polyolefins) or where interfacial agents are added to improve the compatibility at the interface between the constituents of the polymer blend.

Due to its unique interaction with water and body fluids, poly(ethylene oxide) is being considered as a component material for flushable products and fibers. Poly(ethylene oxide) is a commercially available water-soluble polymer that can be produced from the ring opening polymerization of ethylene oxide. Because of its water-soluble properties, poly(ethylene oxide) is desirable for flushable applications. However, there is a dilemma in utilizing poly(ethylene oxide) in flushable applications. Poly(ethylene oxide) resins of low molecular weights, (for example, 200,000 g/mol.) have desirable melt viscosity and melt pressure properties for extrusion processing but cannot be melt processed into fibers due to their low melt elasticities and low melt strengths. Poly(ethylene oxide) melt extruded from the spinning plates on fiber spinning lines resists drawing and is easily broken. Poly(ethylene oxide) resins of higher molecular weights, (for example, greater than 1,000,000 g/mol) have melt viscosities that are too high for melt processes for fiber-spinning. These factors make conventional poly (ethylene oxide) not processable for fiber making by conventional melt extrusion processes.

Poly(ethylene oxide) resins do not form fibers using conventional melt fiber-making processes. For purposes of this application, the term "fiber" refers to filaments or threads or filament-like or thread-like structures with diameters of about 100 microns or less. Conventional poly (ethylene oxide) resins can only be melt processed into strands with diameters in the range of several millimeters. Therefore, poly(ethylene oxide) compositions with appropriate melt elasticities and melt strengths are desired.

In the personal care product industry, flushable meltspun fibers are desired for commercial viability and ease of disposal. Poly(ethylene oxide) fibers have been produced by a solution casting process. However, the prior art has failed to melt process poly(ethylene oxide) fibers using conventional fiber making techniques such as melt spinning. Melt processing techniques are more desirable than solution casting because melt processing techniques are more efficient and economical. Melt processing of fibers is needed for commercial viability. Prior art poly(ethylene oxide) compositions cannot be extruded into the melt with adequate melt strength and elasticity to allow attenuation of fibers. Presently, fibers cannot be produced from conventional poly(ethylene oxide) compositions by melt spinning. Currently available poly(ethylene oxide) resins are not practical for melt extrusion into fibers and for incorporation into personal care products.

There is a need for water-responsive and flushable fibers for use in flushable personal care products, such as flushable diapers, feminine pads, pantiliners, child training pants and adult incontinence pads and briefs.

There is also a need to have flushable fibers comprising a polyolefin and a water-soluble polymer, especially poly (ethylene oxide). In addition to reducing material costs, the presence of a polyolefin in the flushable fiber composition improves melt processability. Many polyolefins can be melt spun into fibers in the prior art. However, no compositions comprising a blend of a polyolefin and poly(ethylene oxide) can be melt spun into fibers by the prior art because of poor melt spinning processability, especially poor melt strength, and poor melt extensibility.

In fiber extrusion processes, such as spunbond and melt-blown processes, the presence of poly(ethylene oxide) in the flushable fiber composition contributes to the water-sensitivity and flushability of the composition.

This invention provides new and useful polymer blend compositions comprising a polyolefin and poly(ethylene oxide) and a process for making water-responsive fiber for use in flushable personal care products.

SUMMARY OF THE INVENTION

Briefly described, the present invention provides fiber compositions which can be used in flushable personal care products. More specifically, this invention provides such compositions which are comprised of modified polypropylene and modified poly(ethylene oxide). These fibers have good ductility with a tensile strain-at-break value which is higher than such value for the polypropylene used in these compositions and substantially higher than the poly (ethylene oxide) used in the fiber compositions of this invention.

The present invention also provides a reactive blending process for the manufacture of such fiber compositions in which polypropylene and poly(ethylene oxide) are modified with a polar vinyl monomer and a free radical initiator in an extrusion apparatus. This process is also referred to as "reactive extrusion". For purposes of this application, reactive extrusion may be defined as conducting or performing chemical reactions during extrusion to form the fiber compositions of the present invention. Free radical initiators, crosslinking agents or other reactive additives can be used during the reactive extrusion process.

Accordingly, an object of this invention is to provide fiber compositions.

Another object of this invention is to provide fiber compositions which comprise modified polypropylene and modified poly(ethylene oxide).

Another object of this invention is to provide water-responsive fiber compositions.

Another object of this invention is to provide water-responsive fiber compositions which comprise modified polypropylene and modified poly(ethylene oxide).

Another object of this invention is to provide fibers which comprise modified polypropylene and modified poly (ethylene oxide).

Another object of this invention is to provide fibers which comprise modified polypropylene microfibers within a matrix of modified poly(ethylene oxide).

Another object of this invention is to provide fibers which comprise modified poly(ethylene oxide) microfibers within a matrix of modified polypropylene.

Another object of this invention is to provide a reactive blending process for the manufacture of fiber compositions.

Another object of this invention is to provide a process for the manufacture of fiber compositions which comprise modified polypropylene and modified poly(ethylene oxide).

A further object of this invention is to provide a process for the manufacture of water-responsive fiber compositions.

A further object of this invention is to provide a process for the manufacture of water-responsive fiber compositions which comprise modified polypropylene and modified poly (ethylene oxide).

A further object of this invention is to provide a process for the manufacture of fibers which comprise modified polypropylene and modified poly(ethylene oxide).

A further object of this invention is to provide a process for the manufacture of fibers which comprise modified polypropylene microfibers within a matrix of modified poly (ethylene oxide).

A further object of this invention is to provide a process for the manufacture of fibers which comprise modified poly(ethylene oxide) microfibers within a matrix of modified polypropylene.

Still another object of this invention is to provide fiber compositions which are useful in flushable personal care products.

Still another object of this invention is to provide fiber compositions having melt rheology which is suitable for the spinning of fibers.

Still another object of this invention is to provide a process for the manufacture of fiber compositions in which polypropylene and poly(ethylene oxide) are modified with a polar vinyl monomer and a free radical initiator.

These and other objects, features and advantages of this invention will become apparent from the following detailed description.

BRIEF DESCRIPTION OF THE DRAWINGS

FIG. 7 shows modified polypropylene microfibers within a continuous phase of modified poly(ethylene oxide).

DETAILED DESCRIPTION OF THE INVENTION

Figure 1:
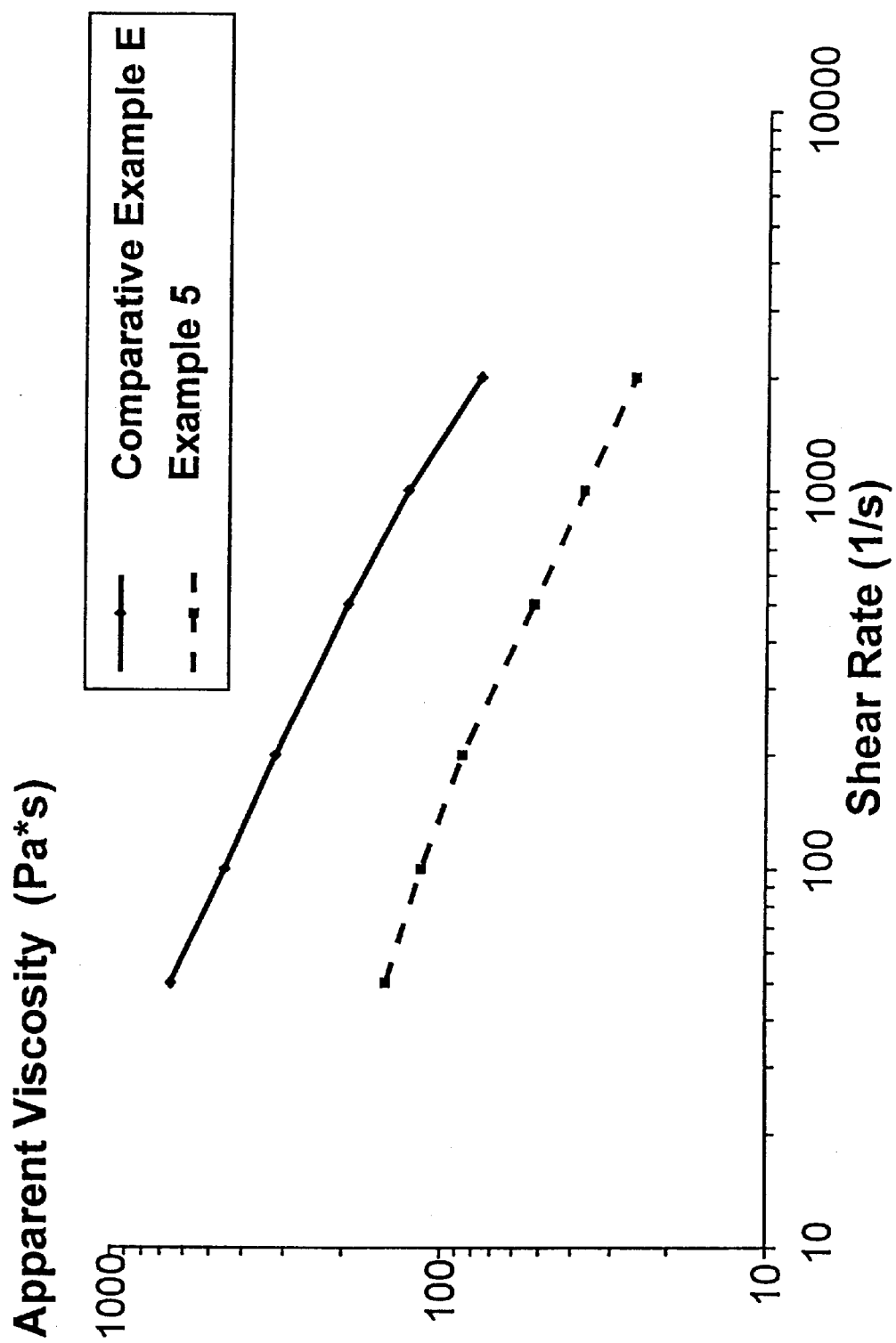
FIG. 1 is a plot of the apparent viscosity versus the shear rate of an unmodified polypropylene/poly(ethylene oxide) blend and a modified polypropylene/modified poly(ethylene oxide) blend to demonstrate the decrease in apparent viscosity of the modified blend (present invention—Example 5) versus the unmodified blend (control—Comparative Example E).

The present invention provides a fiber composition comprising a blend of modified polypropylene and modified poly(ethylene oxide) wherein:

A. the ratio of modified polypropylene: modified poly (ethylene oxide) is from 1:99 to 99:1 by weight;

B. the polypropylene starting material (i.e., prior to modification) has a melt flow rate of about 0.1 to 500 grams/10 minutes at 230° C.;

C. the poly(ethylene oxide) starting material (i.e., prior to modification) has a molecular weight of about 100,000 to about 8,000,000 grams/mole; and D. the blend contains from about 0.1 to about 30 percent, based on the total weight of the modified polypropylene and modified poly(ethylene oxide), of a grafted polar vinyl monomer.

Additionally, the present invention provides a reactive blending process for the manufacture of a fiber composition, wherein the process comprises modifying polypropylene and poly(ethylene oxide) in the presence of a polar vinyl monomer and a free radical initiator, under heat and mechanical shear conditions, wherein:

A. the ratio of polypropylene:poly(ethylene oxide) is from 1:99 to 99:1 by weight;

B. the polypropylene has a melt flow rate of about 0.1 to 500 grams/10 minutes at 230° C.;

C. the poly(ethylene oxide) has a molecular weight of about 100,000 to about 8,000,000 grams/mole as determined by rheological measurements;

D. from about 0.1 to about 30 percent, based on the total weight of the polypropylene and poly(ethylene oxide), of a polar vinyl monomer is added; and E. from about 0.1 to about 2 percent, based on the total weight of the polypropylene and poly(ethylene oxide), of a free radical initiator is added.

The polypropylene useful in this invention includes isotactic, syndiotactic and atactic polypropylene. Additionally, copolymers of propylene with alpha-olefins having 2–10 carbon atoms are useful in this invention. The preferred polypropylenes for this invention are isotactic polypropylene and copolymers of ethylene and propylene.

The fiber compositions of this invention are water-responsive when the ratio of polypropylene:poly(ethylene oxide) is from 1:99 to 50:50 by weight. These fiber compositions have a wide range of water-responsiveness, ranging from water-dispersible to water-disintegratable to water-weakenable.

As used in this application, the term "water-dispersible" means that the composition dissolves or breaks into pieces smaller than a 20 mesh after being immersed in water for approximately five minutes. The term "water-disintegratable" means that the composition breaks into multiple pieces within five minutes of immersion in water and that some of the pieces will be caught by a 20 mesh screen. The term "water-weakenable" means that the composition remains in one piece but weakens and loses rigidity after five minutes of immersion in water and becomes drapeable, i.e. the composition bends without an external force applied thereto when the composition is held by one side at a horizontal position. The term "water-stable" means that the composition does not become drapeable after five minutes of immersion in water and remains in one piece after the water response test.

Accordingly, one aspect of the invention is for a composition of matter comprising a polymer blend having from about 1 to about 99 weight percent of a modified polypropylene and from about 99 to about 1 weight percent of a modified poly(ethylene oxide). Preferably, the blend comprises from about 10 to about 85 weight percent of a modified polypropylene and from about 90 to about 15 weight percent of modified poly(ethylene oxide). More preferably, the blend comprises from about 10 to about 70 weight percent of a modified polypropylene and from about 90 to about 30 weight percent of modified poly(ethylene oxide).

The method of making the polymer blends of this invention includes melt blending the desired weight ratios of a mixture of the polypropylene and poly(ethylene oxide), a polar vinyl monomer and a free radical initiator in an extruder and at a reaction temperature where the polypropylene and poly(ethylene oxide) are converted to a molten state. Accordingly, the polypropylene, poly(ethylene oxide), monomer and free radical initiator can be simultaneously added to the extruder before the polymer constituents, i.e., the polypropylene and poly(ethylene oxide) have been melted. Preferably, the extruder used for melt blending can introduce various constituents into the blend at different locations along the extruder from the feeder port to the die. For example, the free radical initiator, crosslinking agents, or other reactive additives can be injected into the blend before or after one or more of the polymer constituents is melted or thoroughly mixed. More preferably, the polypropylene and poly(ethylene oxide) are added at the beginning of the extruder.

After melting, the monomer is added to the melted polymers and, further down the extruder barrel, the free radical initiator is fed to the melt blend. Although not preferred, the scope of the invention would include simultaneously adding the monomer and free radical initiator into the molten blend of polypropylene and poly(ethylene oxide). It is important to the method of the invention that the polypropylene and poly(ethylene oxide) be melt blended contemporaneously with or before the addition of the monomer and free radical initiator. We believe that the monomer, in the presence of the free radical initiator, grafts onto both the polypropylene and poly(ethylene oxide).

As used herein, the "graft copolymer" means a copolymer produced by the combination of two or more chains of constitutionally or configurationally different features, one of which serves as a backbone main chain, and at least one of which is bonded at some point(s) along the backbone and constitutes a side chain. As used in this application, the term "grafting" means the forming of a polymer by the bonding of side chains or species at some point(s) along the backbone of a parent polymer. (See Sperling, L. H., *Introduction to Physical Polymer Science* 1986 pp. 44–47 which is incorporated by reference herein in its entirety.)

A variety of polar vinyl monomers are useful in the practice of this invention. As used in this application, the term "monomer" includes monomers, oligomers, polymers, mixtures of monomers, oligomers and/or polymers, and any other reactive chemical species which is capable of covalent bonding with polypropylene and poly(ethylene oxide).

Ethylenically unsaturated monomers containing a polar functional group, such as hydroxyl, carboxyl, amino, carbonyl, halo, thiol, sulfonic, sulfonate, etc. are appropriate for this invention and are preferred. Preferred ethylenically unsaturated monomers include acrylates and methacrylates. Particularly preferred ethylenically unsaturated monomers containing a polar functional group are 2-hydroxyethyl methacrylate (HEMA) and poly(ethylene glycol) methacrylates (PEGMA). A particularly preferred poly(ethylene glycol) methacrylate is poly(ethylene glycol) ethyl ether methacrylate. However, we expect that a wide range of polar vinyl monomers would be capable of imparting the same effects as HEMA and PEGMA and would be effective monomers for grafting in the present invention. The amount of polar vinyl monomer relative to the amount of polypropylene and poly(ethylene oxide) may range from about 0.1 to about 30 weight percent, preferably from about 0.1 to 20 weight percent.

Preferably, the amount of polar vinyl monomer should exceed 0.1 weight percent to sufficiently improve the melt processability of the poly(ethylene oxide). More preferably, the amount of polar vinyl monomer should be at the lower end of the range to decrease costs.

Other effective ethylenically unsaturated polar vinyl monomers include poly(ethylene glycol) acrylates, poly(ethylene glycol) ethyl ether acrylate, poly(ethylene glycol) methacrylates with terminal hydroxyl groups, acrylic acid, maleic anhydride, itaconic acid, sodium acrylate, 3-hydroxypropyl methacrylate, acrylamide, glycidyl methacrylate, 2-bromoethyl acrylate, carboxyethyl acrylate, methacrylic acid, 2-chloroacrylonitrile, 4-chlorophenyl acrylate, 2-cyanoethyl acrylate, glycidyl acrylate, 4-nitrophenyl acrylate, pentabromophenyl acrylate, poly(propylene glycol) methacrylate, poly(propylene glycol) acrylate, 2-propene-1-sulfonic acid and its sodium salt, 2-sulfoethyl methacrylate, 3-sulfopropyl methacrylate, and 3-sulfopropyl acrylate. The term "poly(ethylene glycol) ethyl ether (meth)acrylate" as used in this application includes both poly(ethylene glycol) ethyl ether methacrylate and poly(ethylene glycol) ethyl ether acrylate.

This invention was demonstrated in the following examples by the use of PEGMA as the polar vinyl monomer. The PEGMA monomer was supplied by Aldrich Chemical Company, Milwaukee, Wis. under Aldrich Catalog No. 40,954–5. The PEGMA was a poly(ethylene glycol) ethyl ether methacrylate having a number average molecular weight of about 246 grams/mole. PEGMA monomers with a number average molecular weight higher or lower than 246 grams/mole are also applicable for this invention. The molecular weight of the PEGMA can range up to 50,000 grams/mole. However, lower molecular weight are preferred for faster grafting reaction purposes. The preferred range of the molecular weight of the monomers is 246 to 5,000 grams/mole, and the most preferred range is 246 to 2,000 grams/mole. A wide range of polar vinyl monomers as well as a wide range of molecular weights of monomers are expected to be capable of imparting similar effects to the reactive blends and would be effective monomers for grafting and modification purposes.

This invention provides fiber compositions; that is, reactive blends of modified polypropylene and modified poly(ethylene oxide) which can be melt processed into fibers. The prior art has not been able to melt process poly(ethylene oxide) or poly(ethylene oxide)-containing polymer blends into fibers. The prior art has only been able to provide solution-spinning processes to make poly(ethylene oxide) fibers or melt-spinning processes for other types of water-soluble polymers/polymer blends which are melt-processible, such as polyvinyl alcohol. As is well-known in the art, there are significant differences in material properties and end use applications which distinguish and separate fiber-grade and film-grade materials. Typically, a fiber-grade polymer has a significantly lower molecular weight than a film-grade polymer of the same composition.

The particular polypropylene and the conditions for reactive blending must be carefully controlled to produce the desired fiber compositions of this invention. Polypropylene tends to undergo a chain scission reaction in the presence of a free radical initiator, which results in a breakdown of the molecular weight of polypropylene. In this invention, the starting polypropylene and poly(ethylene oxide) are film-grade materials but, after reactive blending, the product is a fiber-grade material in which the molecular weights of both polypropylene and poly(ethylene oxide) have been significantly reduced.

The polypropylene and poly(ethylene oxide) starting materials used in this invention are film-grade materials which cannot be made into fibers without modification (i.e., without substantially reducing their molecular weights). Similarly, a blend of these starting materials cannot be made into fiber. Surprisingly, by subjecting the film-grade polypropylene and film-grade poly(ethylene oxide) to modification with a polar vinyl monomer (or mixture of such monomers) in the presence of a free radical initiator, under the necessary reaction conditions, a fiber composition is obtained. The resulting fiber composition can be processed into fine fibers having a diameter within the range of typical spunbond and meltblown non-woven fibers.

In this invention, we have provided a permanently wettable polypropylene. When fiber compositions having a majority of poly(ethylene oxide) are washed with water, the remaining polypropylene microfibers which have been grafted with the polar vinyl monomer are permanently wettable. Typically in the prior art, wettable polypropylene is not durable, but requires the addition of a topical surfactant to impart initial wettability. However, if the prior art polypropylene is washed several times, the surfactant is washed away and the polypropylene is no longer wettable. The present invention overcomes this disadvantage because the polar vinyl monomer is chemically attached to the polypropylene and is not removed by washing. The prior art has demonstrated this sort of permanent wettability only in batchwise processes in which the surface of a fiber is allowed to react for as long as required to produce the necessary amount of grafting. To the contrary, the present invention is a continuous extrusion process and requires less time for such permanent wettability than the prior art.

Another aspect of this invention provides for a method of making a modified polypropylene and modified poly(ethylene oxide) blend composition. The method provides a single pass, melt reactive extrusion modification of the polypropylene and poly(ethylene oxide). This single step process affords significant advantages over a two step process in which the polypropylene is first modified by grafting a monomer onto the polypropylene backbone, followed by subsequent melt blending with the modified poly(ethylene oxide). The advantages include cost savings, reduced polymer degradation and greater uniformity in the final product.

The method of preparing the blend of modified polypropylene and modified poly(ethylene oxide) using a single pass, melt reactive extruder preferably comprises melting the polypropylene and poly(ethylene oxide) in the extruder and then adding a monomer and a sufficient amount of a free radical initiator to graft from about 1 weight percent to about 100 weight percent of the monomer onto the polypropylene and poly(ethylene oxide).

Reaction vessels, other than an extruder, which are capable of thoroughly blending polypropylene and poly(ethylene oxide) and applying thermal energy can also be used in making the polymer blends of this invention.

A variety of initiators is useful in the practice of this invention. If grafting is achieved by the application of heat, as in a reactive-extrusion process, preferably the initiator generates free radicals with the application of heat. Such initiators are generally referred to as thermal initiators. For the initiator to function as a useful source of radicals for grafting, the initiator should be commercially and readily available, stable at ambient or refrigerated conditions and generate radicals at reactive-extrusion temperatures.

Compounds containing an O—O, S—S or N=N bond may be used as thermal initiators. Compounds containing O—O bonds, such as peroxides, are commonly used as initiators for polymerization. Such commonly used peroxide initiators include: alkyl, dialkyl, diaryl and arylalkyl peroxides such as cumyl peroxide, t-butyl peroxide, di-t-butyl peroxide, dicumyl peroxide, cumyl butyl peroxide, 1,1-di-t-butyl peroxy-3,5,5-trimethylcyclohexane, 2,5-dimethyl-2,5-di(t-butyl peroxy)hexane, 2,5-dimethyl-2,5-bis(t-butylperoxy) hexyne-3 and bis(a-t-butyl peroxyisopropylbenzene); acyl peroxides such as acetyl peroxides and benzoyl peroxides; hydroperoxides such as cumyl hydroperoxide, t-butyl hydroperoxide, p-methane hydroperoxide, pinane hydroperoxide and cumene hydroperoxide; peresters or peroxyesters such as t-butyl peroxypivalate, t-butyl peroctoate, t-butyl perbenzoate, 2,5-dimethylhexyl-2,5-di(perbenzoate) and t-butyl di(perphthalate); alkylsulfonyl peroxides; dialkyl peroxymonocarbonates; dialkyl peroxydicarbonates; diperoxyketals; ketone peroxides such as cyclohexanone peroxide and methyl ethyl ketone peroxide. Additionally, azo compounds such as 2,2'-azobisisobutyronitrile, 2,2'-azobis(2,4-dimethylpentanenitrile) and 1,1'-azobis(cyclohexanecarbonitrile) may be used as the initiator.

The amount of free radical initiator added to the blend of polypropylene and poly(ethylene oxide) is from about 0.1 to about 2 weight percent, preferably from about 0.1 to about 1 weight percent, based on the total weight of the polypropylene and poly(ethylene oxide).

This invention has been demonstrated in the following examples by the use of a liquid, organic peroxide initiator available from Elf Atochem North America, Inc. of Philadelphia, Pa. under the trade designation LUPERSOL® 101, which is a free radical initiator and comprises 2,5-dimethyl-2,5-di(t-butylperoxy)hexane. Other initiators and other grades of the LUPERSOL® initiators may also be used, such as LUPERSOL® 130.

The reaction temperatures effective in making the polymer blends of this invention will be in the range of the melting point of polypropylene to the decomposition temperature of either polypropylene or poly(ethylene oxide), preferably from about 170° C. to about 240° C., and more preferably from about 180° C. to about 220° C.

The fiber compositions of this invention can be melt-processed into fibers (including fibers useful in textile applications, staple fibers, and non-woven fibers, such as spunbond and meltblown fibers). The fiber converting process applicable to this invention can utilize fiber-making apparatus which is standard in the industry for thermally processing a fiber composition into fibers and non-woven fabrics.

The fibers made from the fiber compositions of this invention are typically comprised of two phases—a continuous phase (also referred to as the sea or matrix) and a discontinuous phase (also referred to as islands). The fibers of this invention have an "islands-in-the-sea" type of blend morphology. Either phase can be comprised of modified polypropylene or modified poly(ethylene oxide). The continuous phase is comprised of the majority polymer component, and the discontinuous phase is comprised of the minority polymer component.

To make the fibers of this invention water-responsive and water-sensitive, the continuous phase will be comprised of modified poly(ethylene oxide), while the discontinuous phase will be comprised of modified polypropylene microfibers. The volume fraction for this type of fiber morphology needs at least about 50–99 weight percent of modified poly(ethylene oxide) in the fiber composition. Surprisingly, the diameter of the microfibers is in the range of about one micron or less. Therefore, these fibers are comprised of multiple filaments (i.e., microfibers) of modified polypropylene with a diameter of about one micron or less dispersed in a continuous matrix of modified poly(ethylene oxide). Since modified poly(ethylene oxide) is water-soluble, when the fiber is placed in water the continuous matrix of modified poly(ethylene oxide) dissolves, leaving modified polypropylene microfibers which are wettable because they are grafted with a polar vinyl monomer (i.e., a hydrophilic vinyl monomer). These types of fibers are especially useful in the production of flushable personal care products.

To make the fibers of this invention wettable but not dispersible or soluble in water, the continuous phase will be comprised of modified polypropylene, while the discontinuous phase will be comprised of modified poly(ethylene oxide) microfibers. The volume fraction for this type of fiber morphology needs at least about 50–99 weight percent of modified polypropylene in the fiber composition. Surprisingly again, the diameter of the microfibers is in the range of about one micron or less. Therefore, these fibers are comprised of multiple filaments (i.e., microfibers) of modified poly(ethylene oxide) with a diameter of about one micron or less, dispersed in a continuous matrix of modified polypropylene. Since modified polypropylene is water-wettable but not water-soluble, when the fiber is placed in water the discontinuous phase of modified poly(ethylene oxide) microfibers dissolves, leaving modified polypropylene which is wettable because it is grafted with a polar vinyl monomer (i.e., a hydrophilic vinyl monomer). These types of fibers are especially useful in the production of flushable personal care products.

The present invention is further illustrated by the following examples which are illustrative of preferred embodiments designed to teach those of ordinary skill in the art how to practice this invention and to represent the best mode contemplated for practicing this invention.

COMPARATIVE EXAMPLES A–E

These five examples represent unmodified blends (i.e., control examples) and are designed for comparison to Examples 1–5 which represent the present invention.

A resin blend of the specified weight percent ratio of polypropylene (marketed under the trade designation DS6D81 by Shell Chemical Company) and poly(ethylene oxide) having a molecular weight of about 200,000 g/mol (marketed under the trade designation POLYOX® WSRN-80 by Union Carbide Corp.) was fed to a Haake counter-rotating twin screw extruder (available from Haake Corporation, Paramus, N.J.) at a rate of 5 lb/hr. The extruder had a length of 300 millimeters. Each conical screw had a diameter of 30 millimeters at the feed port and a diameter of 20 millimeters at the die. The extruder had four heating zones set at 180, 190, 190 and 200° C. The screw speed was 150 rpm. The polymer was extruded, cooled in air and pelletized.

For Comparative Example A, the resin blend was 10:90 polypropylene:poly(ethylene oxide). This polymer blend could not be melt processed into fibers.

For Comparative Example B, the resin blend was 20:80 polypropylene:poly(ethylene oxide). This polymer blend could not be melt processed into fibers.

For Comparative Example C, the resin blend was 30:70 polypropylene:poly(ethylene oxide). This polymer blend could not be melt processed into fibers.

For Comparative Example D, the resin blend was 40:60 polypropylene:poly(ethylene oxide). This polymer blend could not be melt processed into fibers.

For Comparative Example E, the resin blend was 60:40 polypropylene:poly(ethylene oxide). This polymer blend could not be melt processed into fibers.

EXAMPLES 1–5

A resin blend of the specified weight percent ratio of polypropylene and poly(ethylene oxide) was fed to a Haake extruder, as described for Comparative Examples A–E, at a rate of 5 lb/hr. The extruder had four heating zones set at 180, 190, 190 and 200° C. The screw speed was 150 rpm. Contemporaneously with the polymer feed to the extruder, poly(ethylene glycol) ethyl ether methacrylate (PEGMA; available from Aldrich Chemical Company, Milwaukee, Wis.) and a free radical initiator, 2,5-dimethyl-2,5-di(t-butylperoxy) hexane (available from Atochem, Philadelphia, Pa. under the trade designation Lupersol 101) were added at 0.5 lb/hr and 0.026 lb/hr, respectively. The polymer was extruded, cooled in air and pelletized.

For Example 1, the blend composition was 10:90 modified polypropylene:modified poly(ethylene oxide). This polymer blend could be melt processed into fibers. The resulting fibers had modified polypropylene microfibers dispersed in a modified poly(ethylene oxide) matrix. The fibers were water-responsive, in that the poly(ethylene oxide) matrix dissolved upon exposure to water, leaving a very weak bundle of modified polypropylene microfibers.

The fibers of this invention can be flushed in a conventional toilet and, therefore, are useful for flushable personal care products, such as flushable diapers, feminine pads, pantiliners, etc.

For Example 2, the blend composition was 20:80 modified polypropylene: modified poly(ethylene oxide). This polymer blend could be melt processed into fibers. The polymer blend morphology and water-responsiveness of these fibers were similar to the 10:90 blend of Example 1.

For Example 3, the blend composition was 30:70 modified polypropylene: modified poly(ethylene oxide). This polymer blend could be melt processed into fibers. The polymer blend morphology and water-responsiveness of these fibers were similar to the 10:90 blend of Example 1.

For Example 4, the blend composition was 40:60 modified polypropylene: modified poly(ethylene oxide). This polymer blend could be melt processed into fibers. The polymer blend morphology and water-responsiveness of these fibers were similar to the 10:90 blend of Example 1.

For Examples 1–4, we observed that with more polypropylene in the blend, the water-responsiveness of the fibers decreased accordingly. The fibers maintained more strength even after the poly(ethylene oxide) matrix was dissolved as the amount of polypropylene was increased in the blends from 10 to 40. This was believed to be due to the increased size and amount of modified polypropylene microfibers left after dissolving the modified poly(ethylene oxide) matrix.

For Example 5, the blend composition was 60:40 modified polypropylene: modified poly(ethylene oxide). This polymer blend could be melt processed into fibers. The resulting fibers were observed to have modified poly (ethylene oxide) dispersed in a modified polypropylene matrix. The fibers were not water-responsive. The surface of the fibers was comprised of modified polypropylene and was wettable by water, but not water-soluble.

Melt Rheology

Melt rheology of Example 5 and Comparative Example E was carried out to demonstrate the difference between polymer blends that are melt processible into fibers and polymer blends that are not melt processible into fibers. Melt viscosities were determined by melt rheology tests performed on a Rheograph 2003 capillary rheometer. The rheometer was operated with a 30/1 mm length diameter die set at 195° C. Apparent viscosities were determined at 50, 100, 200, 500, 1000 and 2000 sec$^{-1}$ to develop rheology curves.

Table 1 and FIG. 1 show the apparent shear viscosity at the specified apparent shear rates.

TABLE 1

| Apparent Shear Rate (s$^{-1}$) | Comparative Example E Apparent Shear Viscosity (Pa * s) | Example 5 Apparent Shear Viscosity (Pa * s) |
|---|---|---|
| 50 | 651 | 147 |
| 100 | 448 | 114 |
| 200 | 318 | 86 |
| 500 | 192 | 52 |
| 1000 | 125 | 37 |
| 2000 | 76 | 26 |

At a shear rate of 1000s$^{-1}$ (approximately the range expected for fiber-spinning), the melt viscosity is observed to drop from 125 to 37, from the unmodified blend to the reactive blend. This relates to a 70% drop in melt viscosity after reactive blending. This drop in melt viscosity is expected to contribute significantly to the fiber melt processability of the material. Each of the other Examples 14 was also observed to undergo a similar drop in melt viscosity compared to the corresponding Comparative Examples A–D at the same polymer blend ratios.

Differential Scanning Calorimetry

Figure 2:
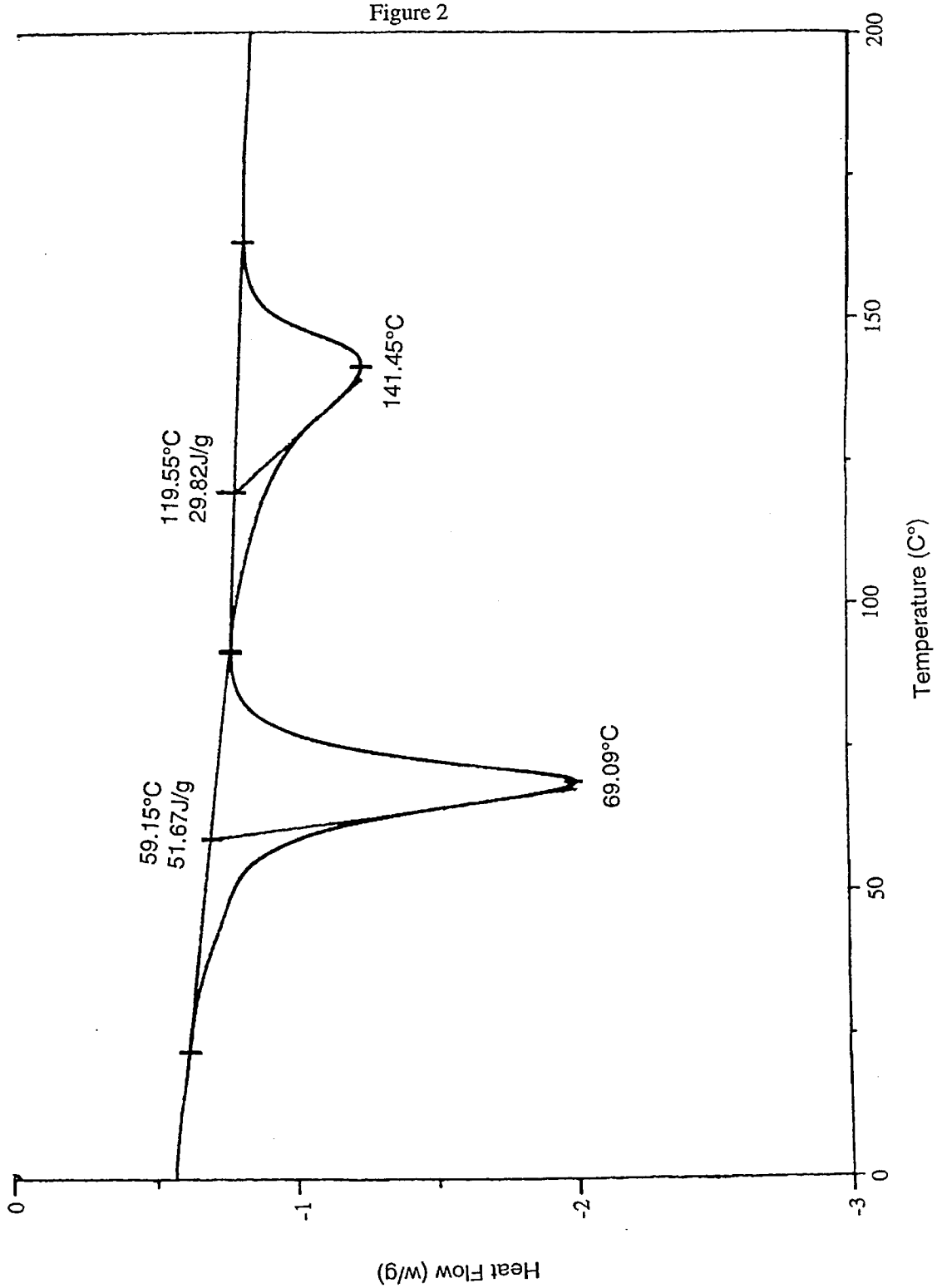
FIGS. 2 and 3 show, respectively, the differential scanning calorimetry thermograms for Comparative Example E (control) and Example 5 (present invention).
Figure 3:
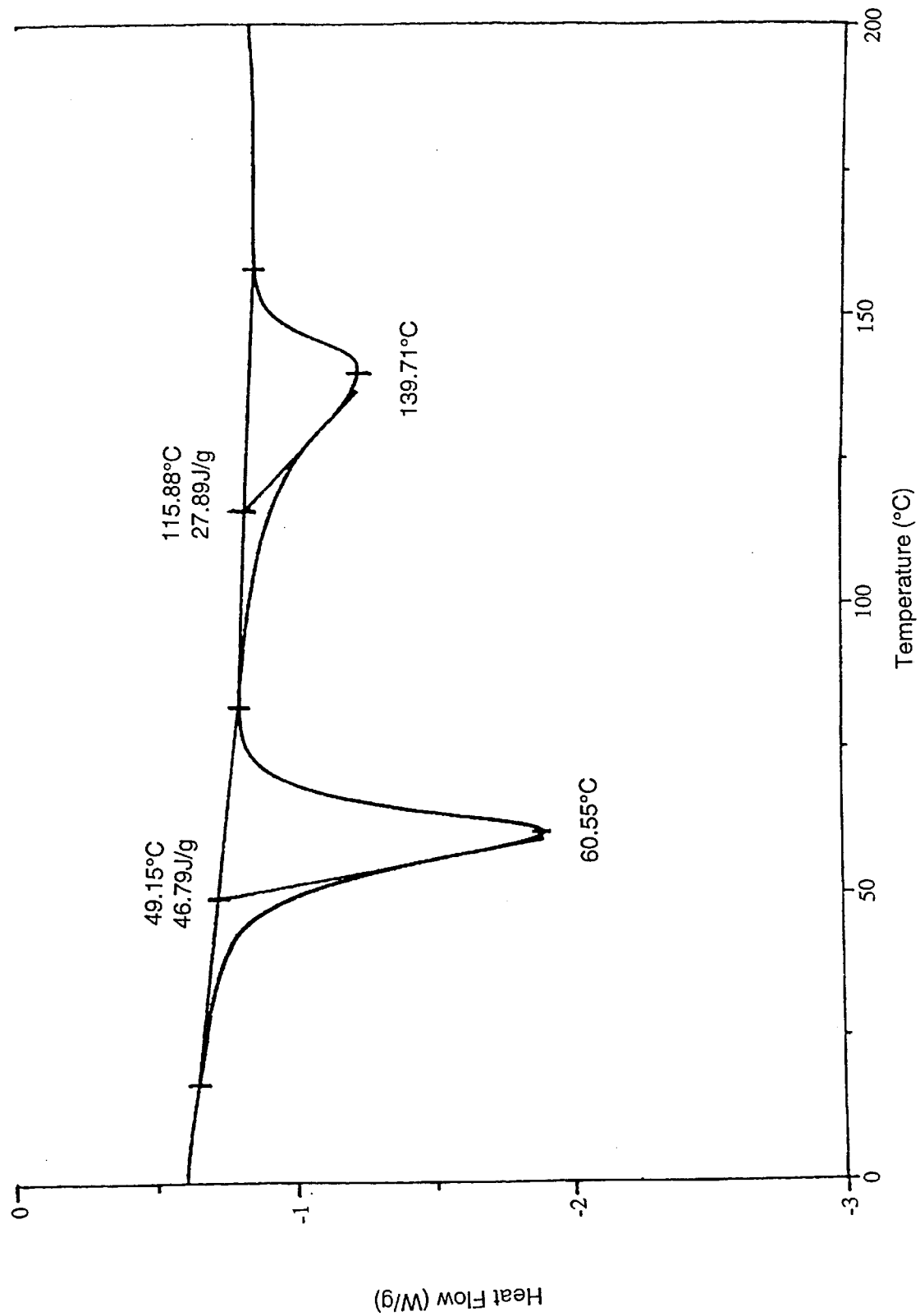

Differential Scanning Calorimetry (DSC) of one set of blends (Example 5 and Comparative Example E) was carried out to demonstrate the melt temperature ($T_m$) and enthalpy of melting (AH) reduction for the reactive blend versus the unmodified blend. The results are shown in FIGS. 2 and 3. The other Examples 1–4 and corresponding Comparative Examples A–D are expected to demonstrate similar thermal properties to other reactive and unmodified blends, due to their similarities in melt properties.

Blend Morphology

Secondary Electron Images (SEI) of the cross-sectional view of the fractured surface and surface morphology of the fibers and one Backscattered Electron Image (BEI) confirming the composition of the dispersed and continuous phases are shown in FIGS. 4A–10. None of the Comparative Examples is shown because these compositions could not be processed into fibers. The structure and morphology are unique to the reactive blends of the present invention.

Figure 4A:
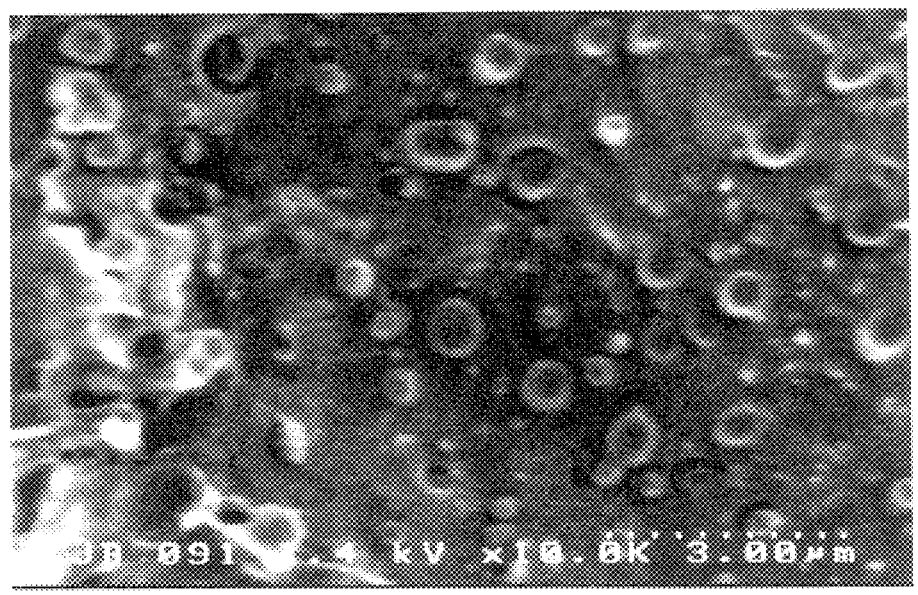
FIGS. 4A and 4B, respectively, show the secondary electron image and backscattered electron image of the cross-section of the fiber made in Example 1, by scanning electron microscopy.
Figure 4B:
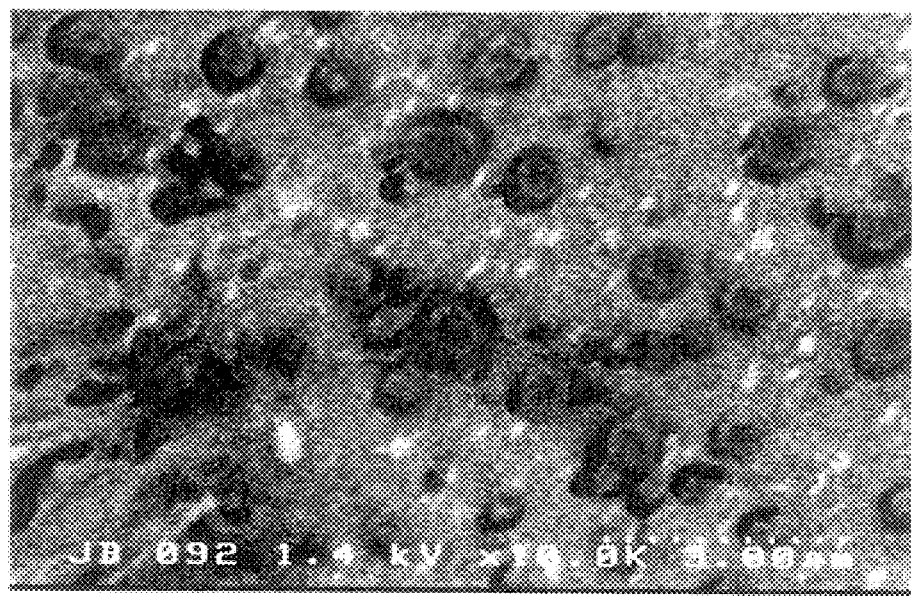
Figure 5A:
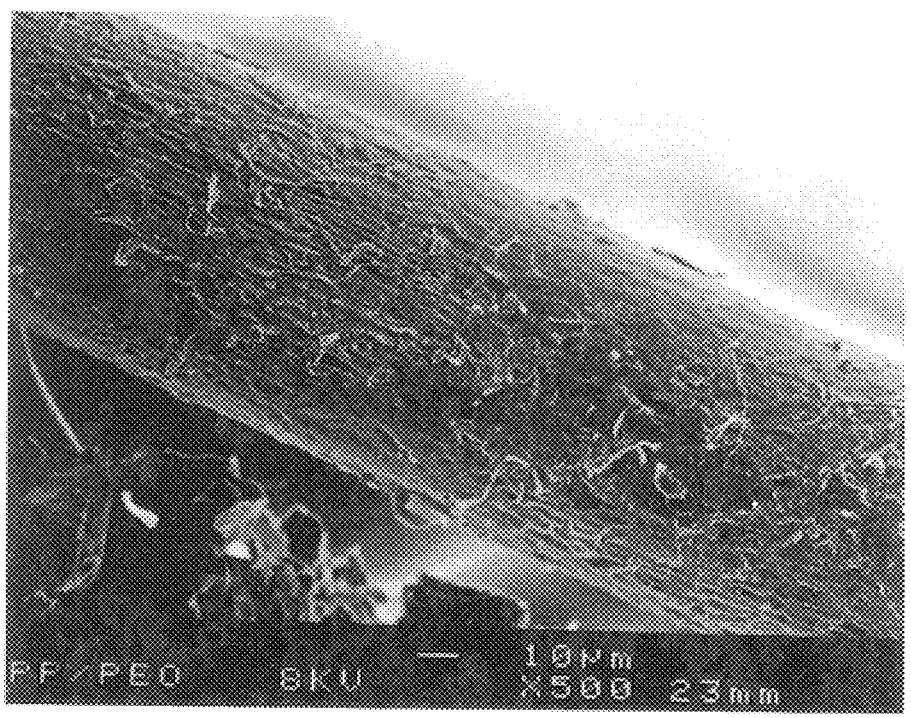
FIGS. 5A and 5B, respectively, show the secondary electron images, at two levels of magnification (500× in FIG. 5A and 3,500× in FIG. 5B), of the fiber surface of the fiber made in Example 2, by scanning electron microscopy.
Figure 5B:
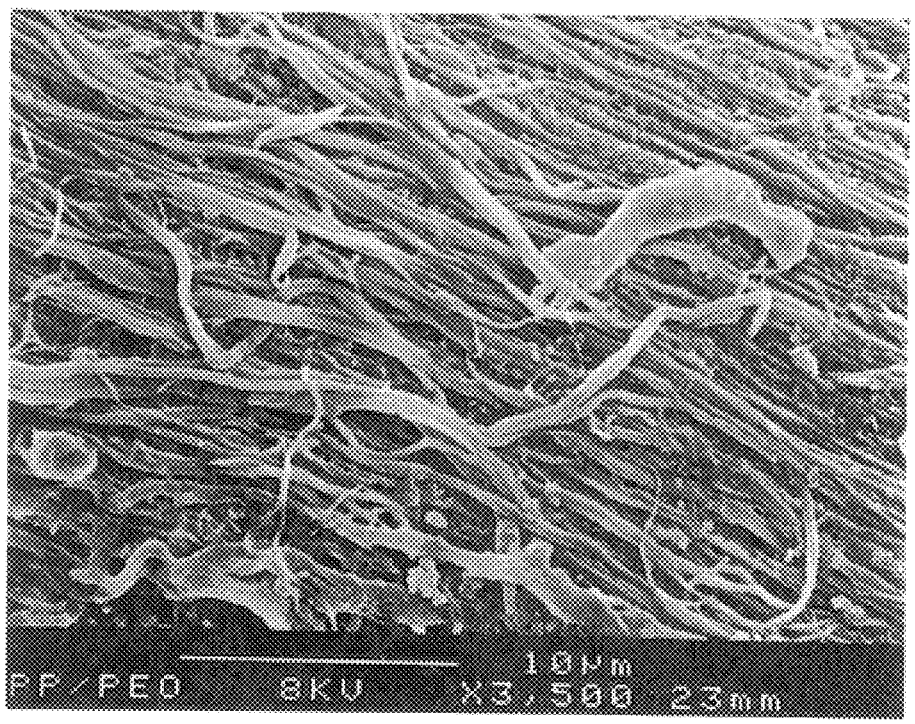
Figure 6A:
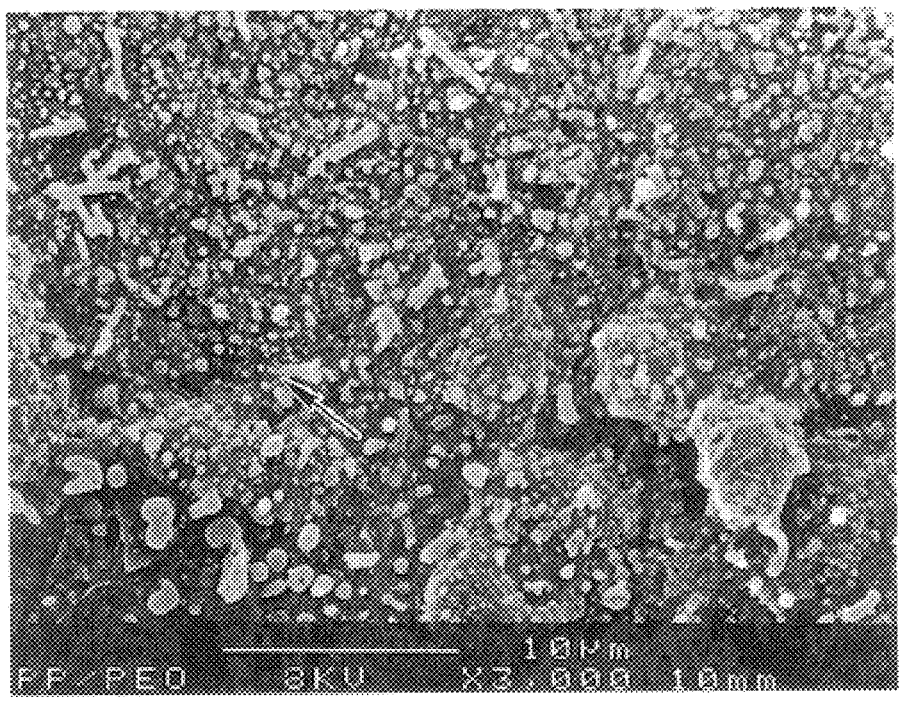
FIGS. 6A and 6B, respectively, show the secondary electron images, at two levels of magnification (3,000× for FIG. 6A and 6,000× for FIG. 6B) of the cross-section of the fiber made in Example 2, by scanning electron microscopy.
Figure 6B:
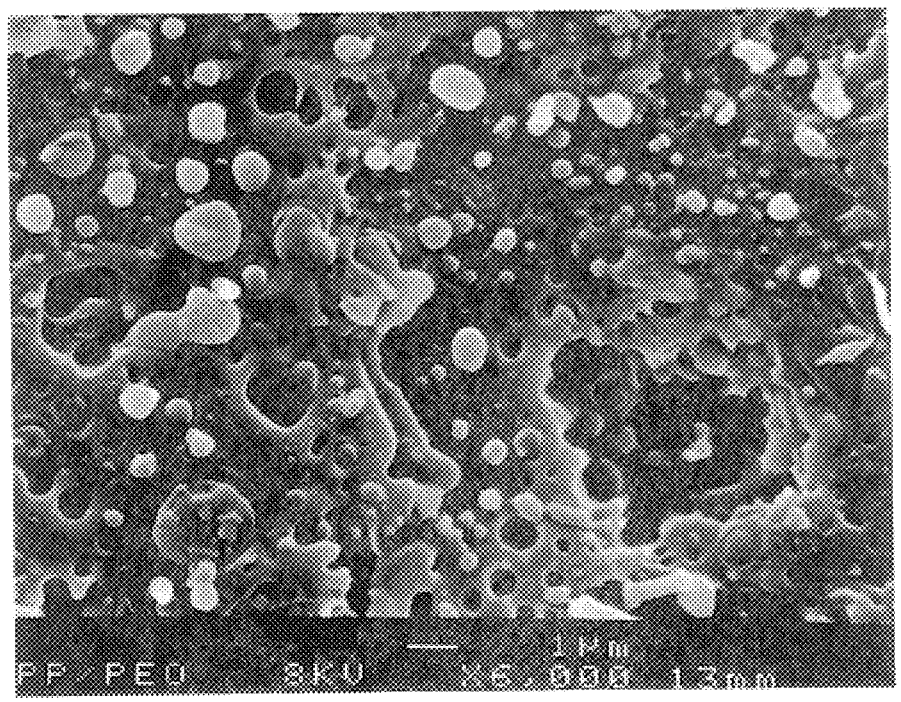
Figure 7:
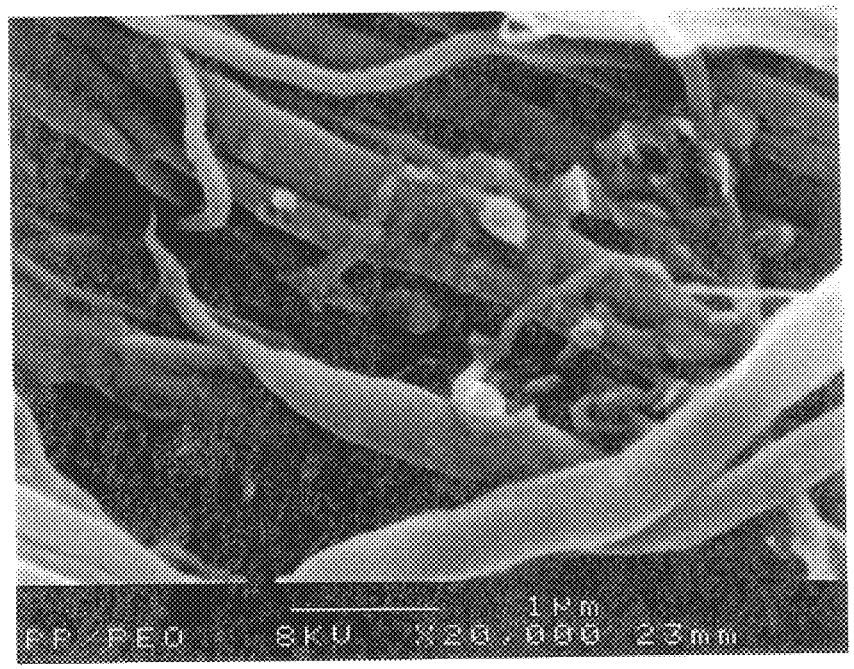
FIG. 7 shows the secondary electron image of the fiber surface of the fiber made in Example 2 at a magnification level of 20,000×, by scanning electron microscopy.
Figure 8A:
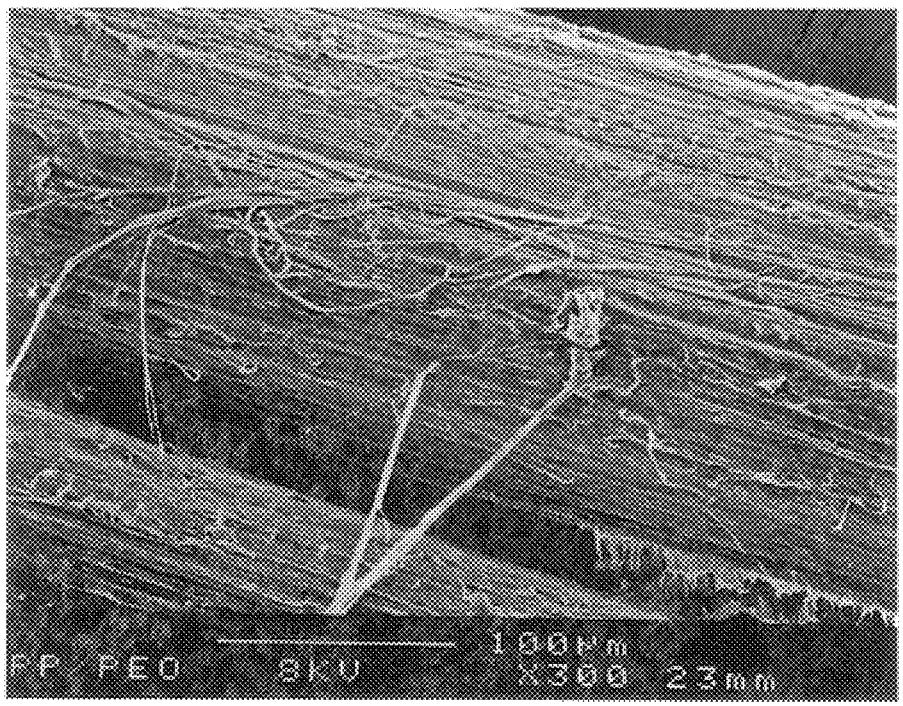
FIGS. 8A and 8B, respectively, show the secondary electron images, at two levels of magnification (300× for FIG. 8A and 2,500× for FIG. 8B), of the fiber surface of the fiber made in Example 3, by scanning electron microscopy.
Figure 8B:
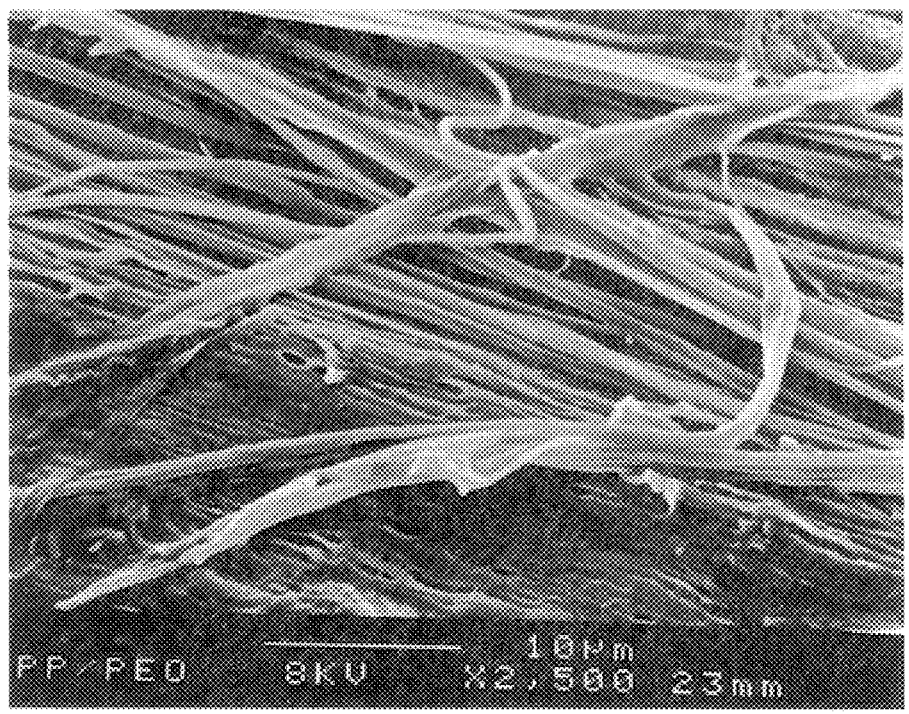
Figure 9:
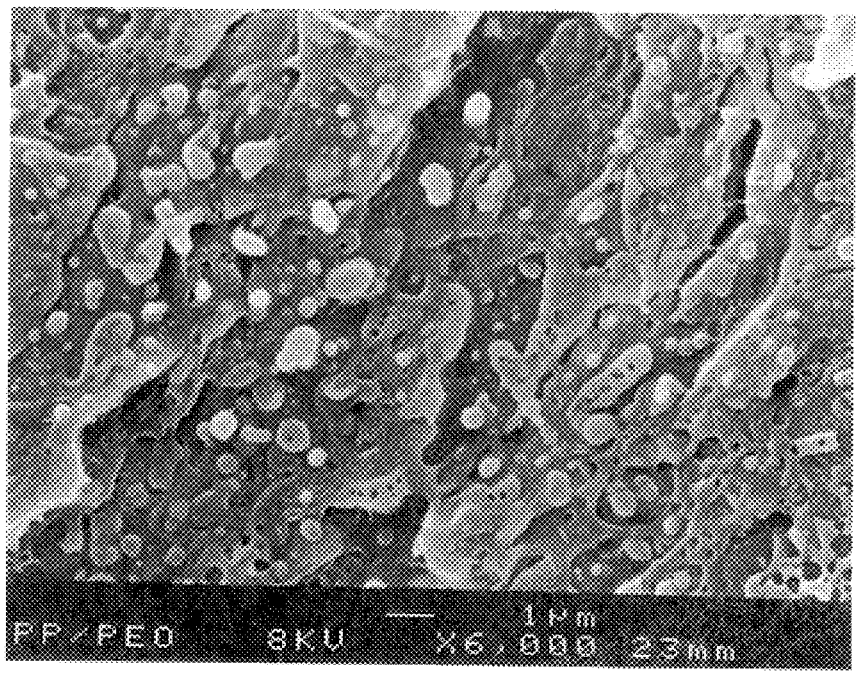
FIG. 9 shows the secondary electron image of the cross-section of the fiber made in Example 3 at a magnification level of 6,000×, by scanning electron microscopy.
Figure 10:
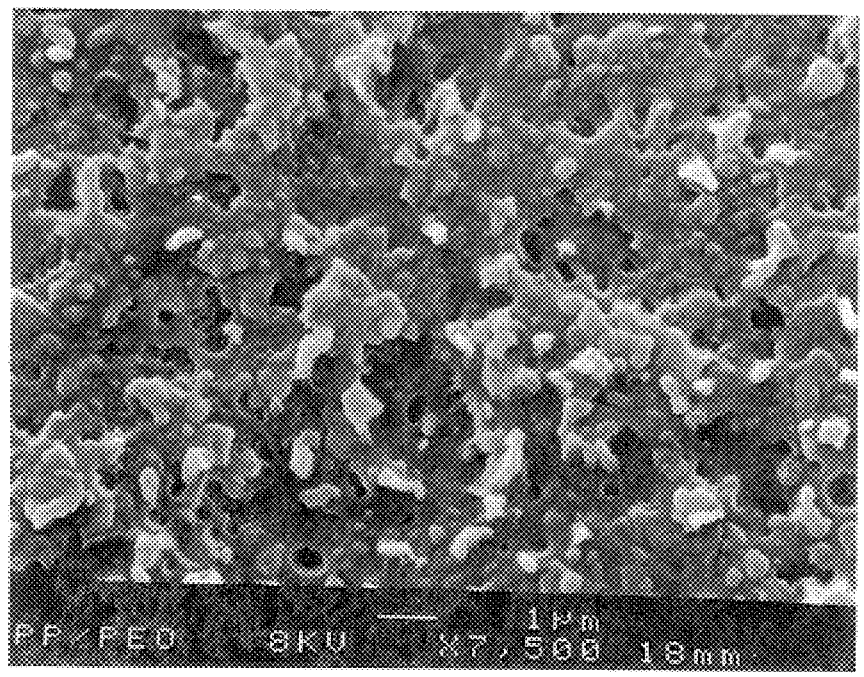
FIG. 10 shows the secondary image of the cross-section of the fiber made in Example 4 at a magnification level of 7,500×, by scanning electron microscopy.

In the SEI photomicrographs, the "microfiber within a fiber" morphology can be observed for 20/80 and 30/70 modified polypropylene/modified poly(ethylene oxide) blends (as shown in FIGS. 5A, 5B, 7, 8A and 8B). This morphology is expected to occur for all blends from 10/90 to about 50/50. A BEI photomicrograph of the 10/90 modified polypropylene/modified poly(ethylene oxide) blend is shown in FIG. 4B. For BEI, the polymer component having a higher average atomic number produces a brighter spot due to higher intensity of backscattered electrons (this distinction in composition cannot be made by SEI since both phases appear similarly on the SEI photomicrographs). The dark spots are modified polypropylene microfibers dispersed in the continuous matrix of bright modified poly(ethylene oxide). This BEI photomicrograph determines the composition of each phase, which will also be true for the phases in the 20/80, 30/70 and 40/60 blends.

Therefore, the BEI can be used to determine the composition of the fiber morphology, but the SEI cannot be used to make the compositional determination.

Due to the lack of water-responsiveness of the 60/40 reactive blend fiber, the phase morphology is expected to reverse from that observed for the blends with a majority of modified poly(ethylene oxide). Thus, a morphology with dispersed poly(ethylene oxide) in a matrix of modified polypropylene would be expected.

This invention has been described in detail with particular reference to certain embodiments, but variations and modifications can be made without departing from the spirit and scope of the invention as defined in the following claims.

What is claimed is:

1. A fiber comprising a fiber composition including polypropylene which has been modified by grafting with a polar vinyl monomer and poly(ethylene oxide) which has been modified by grafting with a polar vinyl monomer, wherein the fiber composition has sufficient melt strength and sufficient melt elasticity for melt spinning into fibers, wherein the fiber composition has an apparent viscosity of less than about 150 Pascal*second at shear rates of not less than about 50 seconds$^{-1}$.

2. A fiber as defined by claim 1, wherein the ratio of modified polypropylene: modified poly(ethylene oxide) is from 1:99 to 99:1 by weight.

3. A fiber as defined by claim 1, wherein the composition contains from about 0.1 to about 30 percent, based on the total weight of the modified polypropylene and modified poly(ethylene oxide), of a grafted polar vinyl monomer.

4. A fiber as defined by claim 1 wherein the polar vinyl monomer is 2-hydroxyethyl methacrylate, poly(ethylene glycol) methacrylate, poly(ethylene glycol) ethyl ether metharcrylate, poly(ethylene glycol) acrylate, poly(ethylene glycol) ethyl ether acrylate, poly(ethylene glycol) methacrylate with terminal hydroxyl groups, acrylic acid, maleic anhydride, itaconic acid, sodium acrylate, 3-hydroxypropyl methacrylate, acrylamide, glycidyl methacrylate, 2-bromoethyl acrylate, carboxyethyl acrylate, methacrylic acid, 2-chloroacrylonotrile, 4-chlorophenyl acrylate, 2-cyanoethyl acrylate, glycidyl acrylate, 4-nitrophenyl acrylate, pentabromophenyl acrylate, poly(propylene glycol) methacrylate, poly(propylene glycol) acrylate, 2-propene-1-sulfonic acid or its sodium salt, 2-sulfoethyl methacrylate, 3-sulfopropyl methacrylate, 3-sulfopropyl acrylate or mixtures thereof.

5. A fiber as defined by claim 4, wherein the polar vinyl monomer is 2-hydroxyethyl methacrylate.

6. A fiber as defined by claim 4, wherein the polar vinyl monomer is poly(ethylene glycol) methacrylate.

7. A fiber as defined by claim 4, wherein the polar vinyl monomer is poly(ethylene glycol) ethyl ether methacrylate.

8. A fiber comprising modified polypropylene microfibers, as defined in claim 1, dispersed in a continuous phase of modified poly(ethylene oxide).

9. A fiber comprising a fiber composition including poly(ethylene oxide) microfibers which have been modified by grafting with a polar vinyl monomer dispersed in a continuous phase of modified polypropylene, wherein the fiber composition has sufficient melt strength and sufficient melt elasticity for melt spinning into fibers, wherein the fiber composition has an apparent viscosity of less than about 150 Pascal*second at shear rates of not less than about 50 seconds$^{-1}$.

10. A fiber as defined by claim 9, wherein the modified poly(ethylene oxide) microfibers have a diameter of about 1 micron or less.

* * * * *